United States Patent [19]

Burstein et al.

[11] 4,009,712

[45] Mar. 1, 1977

[54] FLUTED HIP NAIL IMPLANT SYSTEM FOR ORTHOPAEDIC SURGERY

[75] Inventors: Albert H. Burstein, Shaker Heights; Kingsbury G. Heiple, Cleveland, both of Ohio

[73] Assignee: The Sampson Corporation, Pittsburgh, Pa.

[22] Filed: Aug. 7, 1975

[21] Appl. No.: 602,725

[52] U.S. Cl. .................. 128/92 BA; 128/92 BC; 128/92 EA; 128/92 EC

[51] Int. Cl.² ............................................. A61F 5/04

[58] Field of Search .......... 128/92 R, 92 B, 92 BC, 128/92 D, 92 EA, 92 EB, 92 EC

[56] References Cited

UNITED STATES PATENTS

| | | | |
|---|---|---|---|
| 2,181,746 | 11/1939 | Siebrandt | 128/92 EA |
| 2,789,558 | 4/1957 | Rush | 128/92 EC |
| 3,561,437 | 2/1971 | Orlich | 128/92 BA |
| 3,783,860 | 1/1974 | Burstein et al. | 128/92 BC |

*Primary Examiner*—Louis G. Mancene
*Assistant Examiner*—Robert F. Cutting
*Attorney, Agent, or Firm*—Dennison, Dennison, Meserole & Pollack

[57] ABSTRACT

A fluted hip nail implant system for orthopaedic surgery for use in repair of fractures of the hip or for stabilization of surgically created fractures in the reconstruction of congenital deformaties of the hip. A single piece fluted hip nail with depending bone plate having a specially designed junction between the nail portion and the bone plate adapted to receive instrumentation for use in insertion and removal of the implant. The hip nail portion is formed with flutes terminating in sharp tips for cutting into the bone and providing torsional rigidity. A bone clamp tool having a ball member adapted to be received in a recess on the bone plate assists in clamping the bone plate to a femur to permit application of surgical screws.

14 Claims, 12 Drawing Figures

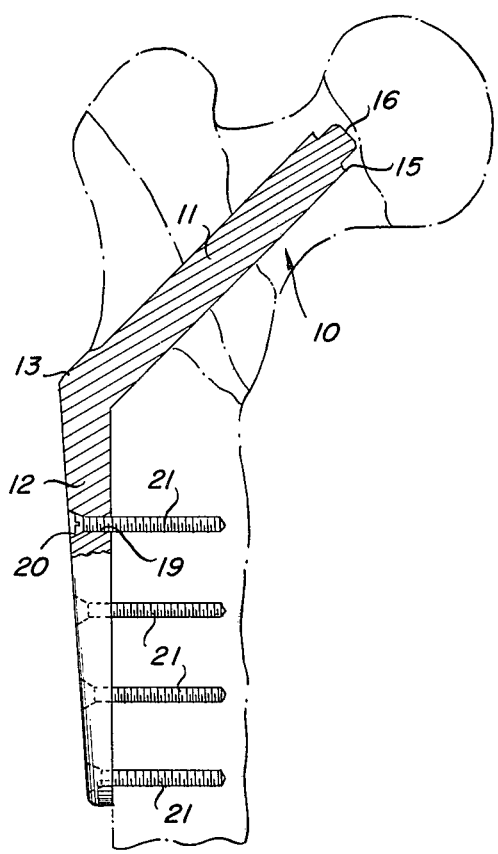
Fig. 1
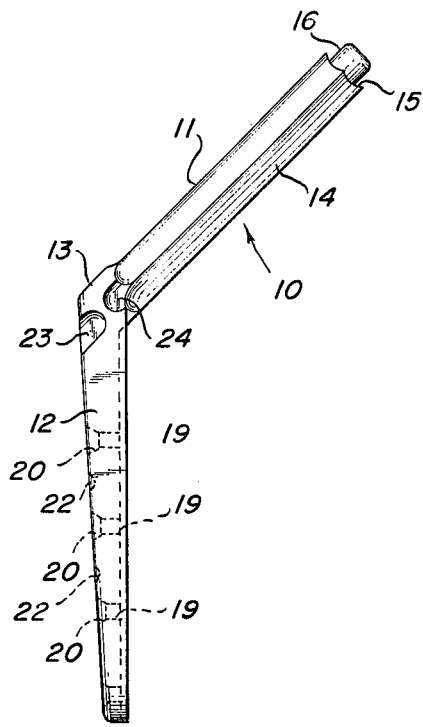
Fig. 2
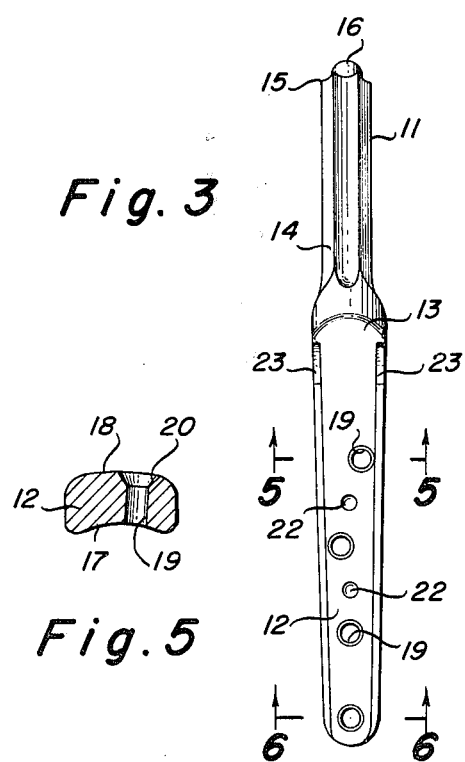
Fig. 3 Fig. 5
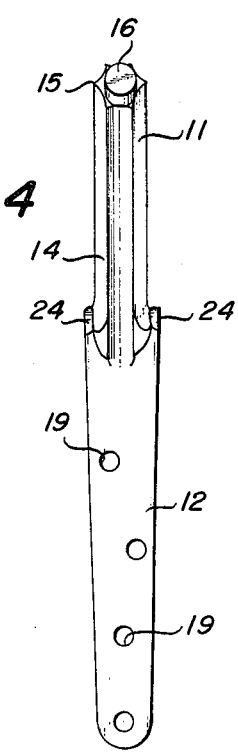
Fig. 4
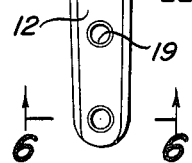
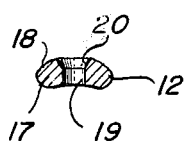
Fig. 6

FLUTED HIP NAIL IMPLANT SYSTEM FOR ORTHOPAEDIC SURGERY

BACKGROUND OF THE INVENTION

The present invention relates generally to orthopaedic implants applied surgically and specifically to a new fluted hip nail primarily intended for use in the repair of fractures of the hip or for use in the stabilization of surgically created fractures in the reconstruction of congenital deformities of the hip principally in children. A single piece fluted hip nail is described including an integral solid nail-plate junction as well as instrumentation for use in the insertion and later removal of the implant.

The principal aim in treatment of patients having intertrochanteric hip fractures, and especially the elderly, is the rapid return in full prefracture activities. Local problems that must be dealt with include proximal femoral instability and deformity as well as pain. Rapid mobilization serves to prevent local skin ulceration, urinary stasis, pneumonia, thromboembolic disease, and other complications arising from long bed confinement.

Accordingly, the treatment of intertrochanteric fractures has conventionally been accomplished by reduction and internal fixation. Most of the prior art fixation techniques serve to alleviate pain and permit the patient to be ambulatory, although they are not generally weight bearing. In some cases the implants are partially weight bearing during assisted ambulation. The elderly patient in most cases does not have sufficient strength or coordination to protect the hip from excessive stress while walking with the assistance of crutches or the like.

The prior art has attempted to provide fixation of the fracture that is so stable that the patient's full weight may bear on the fractured hip. Typical strong nails for this purpose have been developed by E. P. Holt, Jr. (Journal of Bone and Joint Surgery, 45-A: 687–705, June, 1963) and A. Sarmiento (Journal of Bone and Joint Surgery, 45-A: 706–722 June, 1963). Others have suggested altering the positions of the fracture fragments to improve the mechanical resistance of the bone to the disruptive forces during weight bearing. (Dimon et al., Journal of Bone and Joint Surgery, 49-A: 440–450 April, 1967; and Massey, Journal of Bone and Joint Surgery 46-A: 658–690, April, 1964).

The three most common implants presently being used for such fracture reduction and fixation are the Jewett nail, a telescoping screw device, and the Holt nail. Tests on these devices are to be found in the literature; note Journal of Bone and Joint Surgery; 56-A, 899–907, July, 1974; Acta chir. Scandinav. 117: 427–432, 1959. During these tests the Jewett nail showed bending at the fracture site and continued varus angulation at relatively low load levels. Anatomical reduction using a telescoping screw device maintained the desired neck shaft angle until the screw had completely telescoped. Continued loading then produced bending at the screw plate angle. When a femur fixed with a Holt nail was tested, the load rose rapidly and then dropped off as a result of fracture of the trabeculae in contact with the nail. Further loading resulted in bending of the nail.

The forces acting on the head of an adult femur are quite surprising at first glance. When standing on one leg the force would be 2 and ½ times body weight; for walking, five to six times body weight. Hence, for a 60 kg man it will be appreciated that the femoral head would be exposed to forces in the range of 150 to 300 or more kg. With regard to the proximal end of the femur, studies show a capacity before fracture of 500 kg for the elderly and 1000 kg for the young. Any implant designed for use in intertrochanteric fracture treatment must therefore approach these levels. Most of the internal fixation devices which have been tested have a failure strength of only 100 to 200 kg.

Hip nails actually undergo two types of bending under the application of force; one is elastic and the other is a permanent type of deformation. When forces act on a nail below its elastic limit, the nail will bend and then when pressure is removed, it will resume its original configuration with no measurable permanent deformation. If the elastic limit is surpassed, however, a permanent deformation will result.

For a more detailed discussion of implant systems with regard to stress parameters, reference may be made to "Biomechanical Principles of Intramedullary Fixation" Clinical Orthopaedics No. 60, 1968, 13–20.

The unitary one-piece fluted hip nail which is the subject of this invention provides significantly improved bending strength in the fixation of fractures as well as in the stabilization of surgically created fractures in hip reconstructive surgery on children. Additionally, the new nail, by virtue of its fluted design, provides improved torsional stability.

A review of the prior art indicates that present implant devices of this type either severely compromise their fatigue and ultimate strength by the provision of central driving recesses and/or central cannulation to facilitate insertion, or sacrifice stability in order to eliminate the need for driving surfaces.

All known trochanteric implants provided with fins or vanes to provide rotational stability, such as Price, U.S. Pat. No. 2,627,855, employ a central bore for driving which seriously weakens the device both with regard to fatigue life and the ultimate load carrying capacity.

The prior art devices which are devoid of such a central bore for driving and extraction forego the rotationally stabilizing flutes or fins in order to facilitate insertion because such projections require forcible insertion into the bone. Therefore, most of the devices now in use employ a central bore which unfortunately is at the central or high stress portion of the nail and support plate.

It should be further noted that most known implants have a small or sharp frontal area for ease in insertion into the bone, and the few that are blunt lack rotational stability.

With regard to instrumentation, the existing implants such as Collison, U.S. Pat. No. 2,612,159, have smooth surfaces in the areas between the screw holes of plate portions which fit against the upper end of the femur which makes it extremely difficult to clamp this portion to the bone without slipping of the clamping instrumentation which would create surface damage to the plate or which could require the instrumentation to obstruct one or more of the screw holes.

OBJECTS AND SUMMARY OF THE INVENTION

Bearing in mind the above problems inherent in the prior art, it is an object of this invention to provide a fluted hip nail implant having sufficient static and fatigue strength to internally stabilize fractures or osteotomies of the proximal end of the femur, neck, intertrochanteric, peritrochanteric and subtrochanteric regions to allow them to heal or alternatively to provide maximum stability to fractures that may never heal.

It is a further object of this present invention to provide a one-piece hip nail implant having resistance to penetration of the femoral head while maintaining rotational control.

Still a further object of the invention relates to configuration of the surface of a plate portion of a hip nail so that the same may be clamped to the femur during insertion without creating surface damage or obstructing screw holes in the plate during drilling procedures.

Yet another object of the invention is the provision of a one-piece implant for immobilizing a fracture of the neck of a femur which is of simple design and which is relatively simple to install and remove and which is exceedingly strong and safe in use.

According to the present invention, there is provided a one-piece implant including a solid fluted rod or nail having relatively sharp cutting points on the ends of the flutes and a reduced cross-section, smooth, blunt tip extending beyond the flutes to prevent cut-out. An integral depending nail plate having screw holes is provided for attachment by screws to the surface of the femur and is further provided with ball seats to accept the jaw of clamp instrumentation herein described. The critical junction of the nail plate and the rod is specially designed to provide exceptional bending strength and includes nonweakening buttresses for reception of a special impaction and extraction tool.

BRIEF DESCRIPTION OF THE DRAWINGS

In order that the invention may be more fully understood, a preferred embodiment in accordance therewith will now be described by way of example with reference to the accompanying drawings in which:

FIG. 1 is a vertical sectional view of the new implant secured in position in a fractured neck of a femur which is shown in dotted lines;

FIG. 2 is a side elevation of the implant;

FIG. 3 is a front elevation of the implant;

FIG. 4 is a rear elevation of the implant;

FIG. 5 is an enlarged horizontal section through the bone plate portion of the implant taken on line 5—5 of FIG. 3;

FIG. 6 is an enlarged section similar to FIG. 5, but taken on line 6—6 of FIG. 3;

DESCRIPTION OF THE PREFERRED EMBODIMENT

Figure 7:
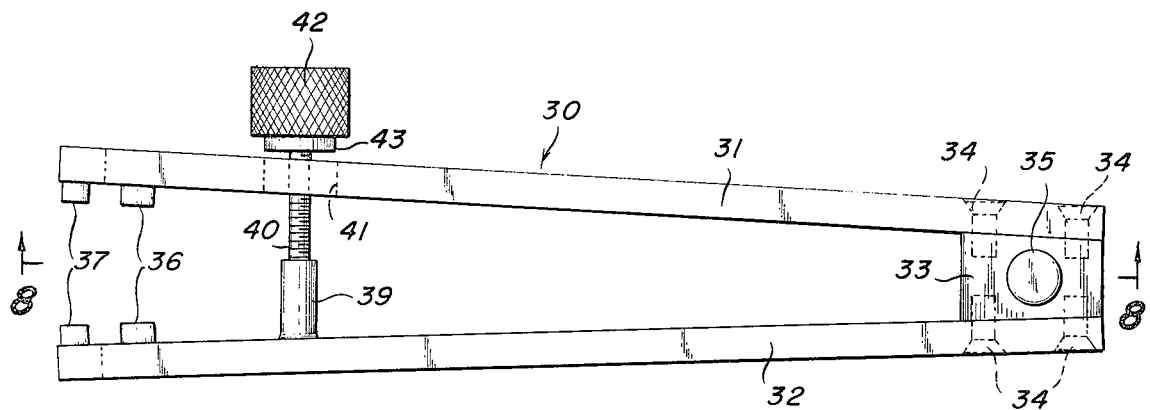
FIG. 7 is a top plan view of the impactor/extractor instrumentation employed with the implant.

Referrring to the drawings wherein like reference characters represent like parts, the hip nail of the present invention is shown generally at 10 and includes a hip nail portion 11 and a bone plate portion 12 angularly related to each other and meeting at a junction 13. The entire implant may be cast, forged and machined from a single block of metal which is compatible with the human body. While titanium or various types of stainless steel are acceptable, we have found that Titanium type 6 Al 4v Eli; ASTM F-136 is ideal for this purpose.

The angle 6 included between nail portion 11 and plate portion 12 may vary dependent on use. We have found that an angle of about 135° is suitable for most fracture use although with pediatric hip nails, angles of 145° and 115° are preferable for valgus and varus osteotomies respectively.

With respect to the hip nail portion 11, the length thereof may be from 2.5 to about 15.2 cm. The major length of hip nail portion 11 is provided with a plurality of longitudinally extending flutes or vanes 14 commencing with a smooth transition from junction 13 and terminating in relatively sharp points 15 defined by a sharply angled face. These points 15 serve to cut into the bone during insertion by impaction into a predrilled bore, and provide a means for gripping the bone both proximal and distal to the fixation site. This mechanical locking provides significant torsional stability.

To increase the resistance of the nail portion to penetration of the femoral head, the end thereof is provided with a short blunt head 16 of slightly reduced cross-section, sufficient however to prevent further bone penetration once insertion is completed.

The bone plate 12 is tapered slightly from junction 13 to its tip and is rounded on its inner and outer faces 17 and 18 in order to properly conform to the femur surface. It will be noted from an examination of FIGS. 3 and 4 that the width of the bone plate adjacent the junction 13 is greater than the width of the fluted hip nail portion.

Figure 10:
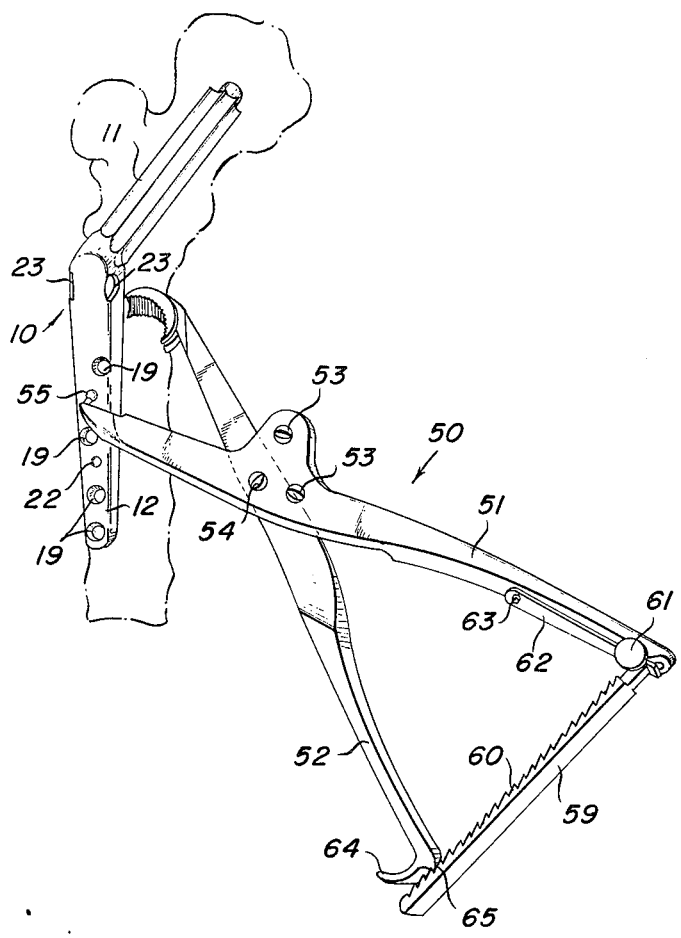
FIG. 10 is a perspective view of the implant in place in a femur neck showing the application of our new bone plate clamping tool prior to drilling of the femur.

In order to secure the bone plate to the femur, a plurality of screw holes 19 are drilled therein and countersunk as at 20. As best seen in FIGS. 3 and 10, the holes 19 are staggered and any number may be provided, although four, five or six-hole plates are preferable for an adult implant and two or three holes for pediatric use. When more than three holes are employed, only the top three are staggered or offset. After the bone plate has been securely clamped into close contact with the femur, as later described herein, conventional bone screws of a compatible metal 21 are inserted into the holes 19 and brought up tight with a surgical screw driver.

To assist in clamping the bone plate to the femur without marring the surface of the implant, one or more hemispherical depressions 22 are formed on the outer face 18 of the plate which are engaged by the new clamp instrumentation also later described herein.

The junction 13 of our new implant has been specially designed for use of our new impactor/extractor instrumentation. Since this is a critical area of the implant with regard to stress application, it is the most massive section of the entire appliance. The material provides a buttress so that there are two semicircular surfaces provided on each side of the junction from the outer face 18 as shown at 23. These buttresses are made parallel to the longitudinal axis of the nail portion 11. A generally similar pair of extractor buttresses 24 are formed on the inner side of junction 13 also parallel to the nail portion longitudinal axis. These buttresses accommodate matching stubs or protuberances on the impactor/extractor instrumentation later described so that insertion and retraction forces may be applied to the implant in its areas of maximum strength.

Figure 8:
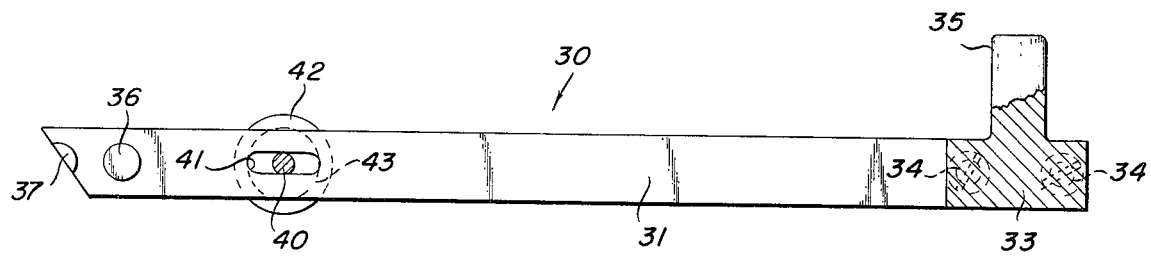
FIG. 8 is a sectional view of the impactor/extractor tool taken on line 8—8 of FIG. 7.
Figure 9:
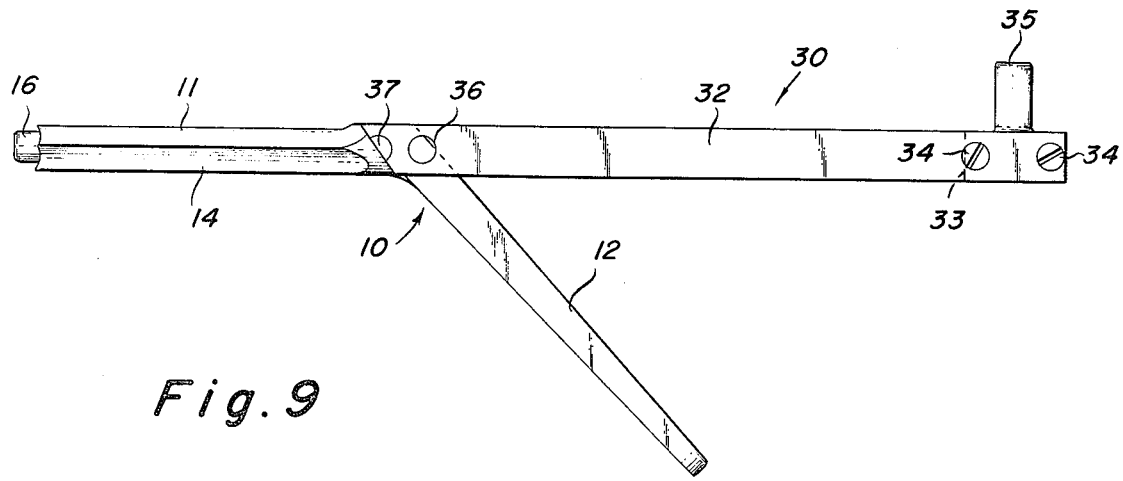
FIG. 9 is a side elevation of the fluted nail implant with the impactor/tool attached thereto.

Our new impactor/extractor instrumentation for use in facilitating insertion and retraction of the implant is shown generally at 30 in FIGS. 7–9 and includes a pair of spring arms 31 and 32 connected at their rear ends to a solid spacer block 33. Screws 34 are preferably used to fasten the arms to the block. An integral post 35 of cylindrical shape extends upwardly from the top of the block. Both the rear face of block 33 and the outer surface of post 35 may be struck with a surgical mallet in insertion or removal of the implant.

On the inner faces of arms 31 and 32, a pair of opposed impactor stubs 36 are formed which are coaxial and project inwardly toward each other. These stubs are adapted to be received within and engage in the impactor buttresses 23 and to this end are cylindrical so as to abut the semicircular front configuration of these buttresses. A second pair of opposed stubs 37 of semicylindrical configuration are formed at the angled ends of arms 31 and 32 and are adapted to be received within and to engage in the extractor buttresses 24 of the implant. It will be understood that the rear curved surfaces of the stubs 37 abut against the curved faces of the buttresses 24.

The arms 31 and 32 are sufficiently spaced apart at their free ends as shown in FIG. 7 so that they may be placed about the implant 10 with ease and a screw arrangement is provided to force or tension the arms together so that the stubs 36 and 37 are securely fastened within the buttresses 23 and 24 as shown in FIG. 9. An inwardly threaded boss 39 is formed on the inner face of arm 32 spaced rearwardly of stubs 36. An elongated clearance slot 41 is formed through the arm 31 to receive screw shaft 40. A knurled thumb knob 42 is secured on the screw shaft along with a washer 43, the free end of screw 40 being threadedly received within boss 39. Turning of the thumb knob 42 will therefore force arms 31 and 32 together as noted above.

After the impactor/extractor instrumentation is attached to the implant, the nail portion 11 may be forced into a predrilled bore in the femur. A series of sharp blows with a mallet on the rear face of block 33 or post 35 will transmit the force through the instrumentation to the strongest areas of the implant junction 13. Impaction is continued until the nail plate portion is immediately adjacent the femur. At this time the impactor/extractor instrumentation may be removed and the bore plate clamp instrumentation applied.

It will be apparent that if for any reason it is desired at this time or later in the operative procedure to remove the implant, the impactor/extractor instrumentation may again be applied. Percussive force may then be placed against the inner face of post 35 to remove the implant 10.

When it is desired to secure the bone plate to the shaft of the femur, the bone plate clamp instrumentation 50 is utilized. This device comprises a pair of crossed lever arms 51 and 52 having adjustable fulcrum or pivot means at their area of crossing to enable use with femurs regardless of size. To this end arm 51 is formed with a widened projection shown in FIG. 11 which is provided with a plurality of adjustment holes 53 to receive a pivot pin 54 carried by arm 52. The holes are circular on the top face but elliptical adjacent the bottom face thereof. Pin 54 is generally cylindrical however its top surface is elliptical so that upon proper alignment it may be received in either of the holes 53.

Thereafter, slight movement of the arms 51 and 52 with respect to each other will cause the elliptical opening to go out of alignment with the elliptical head of pin 54 permitting rotation but obviating separation of the arms.

Figure 11:
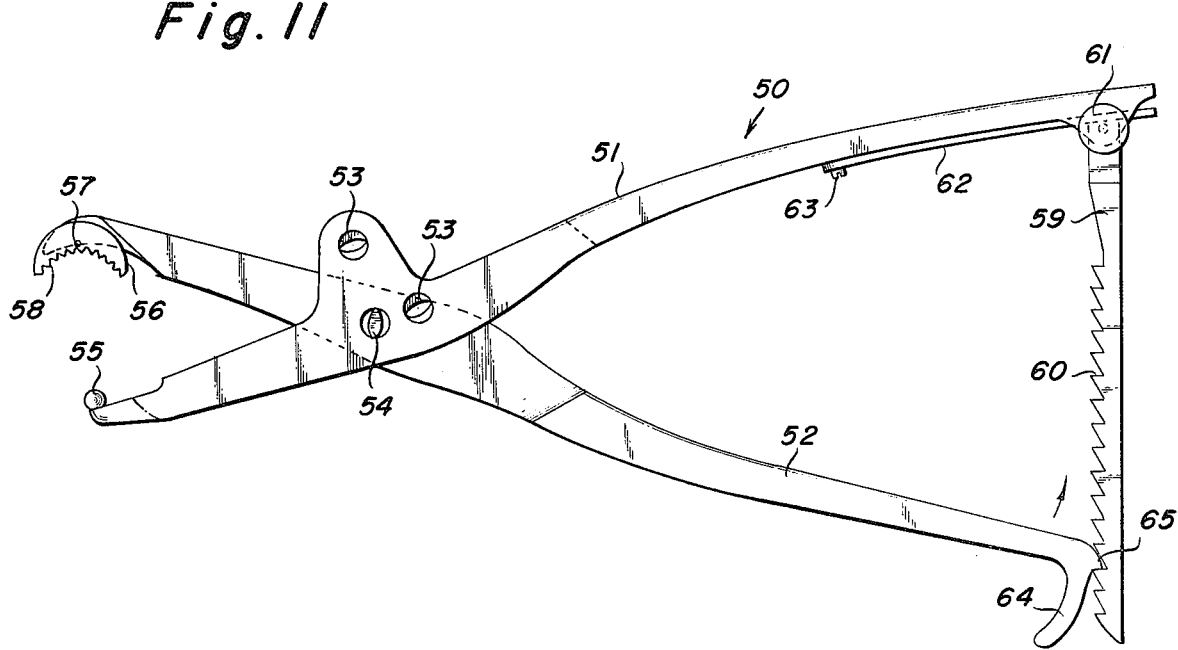
FIG. 11 is a plan view of the bone plate clamping instrumentation.

At its free end, arm 51 has a ball member 55 mounted thereon adapted to be received within one of the hemispherical depressions 22 on the outer face 18 of bone plate 12. Arm 52 at its free end receives an arcuate bone clamp 56 pivoted thereto at 57. Arm 52 may be recessed in this area as shown in FIG. 11 to permit clamp 56 to swing to a limited degree. Serrations 58 are formed on the inner face of clamp 56 to ensure a firm purchase on the femur.

Adjustable locking means of the conventional hemostat type are provided at the other ends of the arms 51 and 52 so that selective compression of the clamp instrumentation about the bone may be maintained during drilling of the screw holes 19 and application of screws 21. Ratchet bar 59 having a series of toothed steps 60 is pivotally fastened to arm 51 as at 60. A leaf spring 62 secured to arm 51 by a screw 63 serves to maintain the bar 59 in proper position, all as well known in the art of medical instrumentation. The free end of arm 52 is formed with a pawl 65 configured to cooperate and lock within the toothed steps 60. Adjacent to pawl 65 is a depending curved finger guard 64.

The manner of applying the bone plate clamp will be apparent from a study of FIG. 10. Clamp 56 is placed about the rear face of the femur with the ball member 55 placed in one of the depressions 22 of the bone plate. Squeezing of arms 51 and 52 is commenced until the bone plate is drawn up snugly against the femur and this position will be maintained by the locking of pawl 65 within the toothed steps 60 until the bone plate has been secured in place by screws 21. Thereafter, slight squeezing pressure is applied on arms 51 and 52 and bar 59 is then released by pivoting the same outwardly, releasing the locking action and allowing removal of the bone plate clamping instrumentation. It will be observed that the bone plate clamp permits unobstructed screw fixation without damage to the plate surface.

Figure 12:
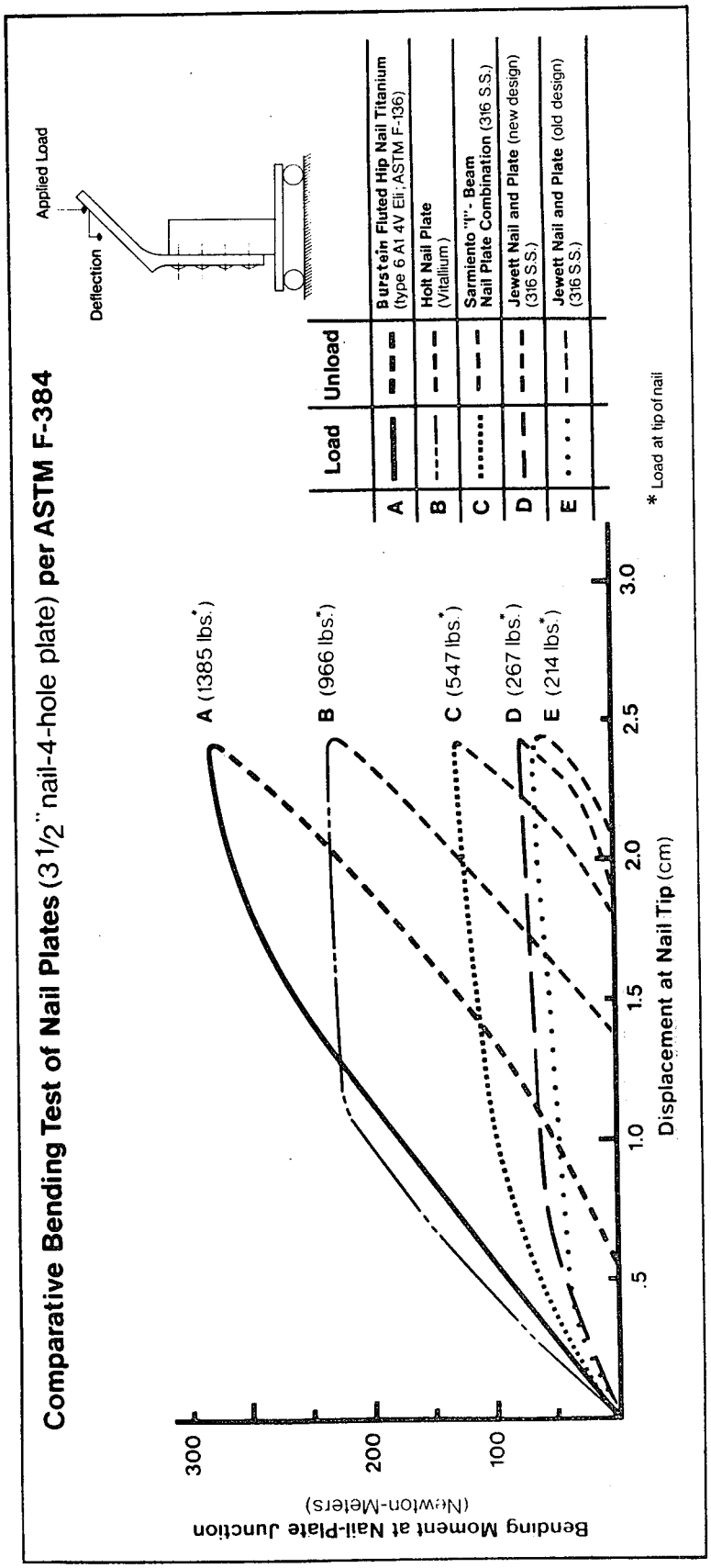
FIG. 12 is a graph depicting results of bending tests of prior art hip nails and the nail of the present invention.

Comparative bending tests of our new implant and selected commonly-used hip nail implants have been conducted in order to show the improved strength qualities of the new nail and the same are graphically illustrated in FIG. 12. These tests obtained the relative static strength characteristics, stiffness and mode of plastic deformation of the implant test specimens. Our new implant was tested against a Vitallium Holt nail, a Sarmiento I Beam Nail plate combination, and old design Jewett Nail and plate, and a new design Jewett Nail and plate. All specimens included a 3½ inch (8.9 cm) nail and a four hole bone plate. The test specimens were chosen from commercial sources and the tests were performed in accordance with the proposed standard test procedure of the F-4 Committee on Surgical Implants of the American Society for Testing and Material. The graph depicts the plot of nail tip displacement in centimeters against the bending moment of the nail plate junction in Newton-meters and the apparent merits of our new implant will be apparent.

In order to utilize the strength and rigidity of this implant in osteosynthesis, it is necessary that loads be transmitted to the nail from the bone under both torsional and bending loading. In bending, the nail is readily loaded wherever it comes into contact with cortical bone. Rigidity at the fracture site will depend on the properties of the nail and its fit in the canal. However, in the case of torsional loading it is necessary for the nail to have intimate contact with the cortical bone so that the shear stresses may be built up between the nail and bone and torque transmitted from one fragment to another. This contact is achieved herein by the application of flutes on the nail portion.

The strength of the implant is of course a measure of the maximum loading that can be applied to the structure before failure occurs and there are three major causes or types of such failure: namely, plastic failure, brittle type fractures, and fatigue fractures. Plastic failure is dependent to a great degree on the type of material chosen for the implant and can be predetermined by investigation of the stress-strain curves for various metals. Brittle type fractures occur in regions of stress concentrations such as notches and other discontinuities and are avoided here by careful design especially in the critical nail-bone plate junction area. Since this junction or transition section must also incorporate means for both driving and extracting the implant, external surfaces to cooperate with instrumentation were incorporated therein. These surfaces or buttresses are located at the neutral bending axis so as to prevent damage to any high stress region of the junction during insertion or removal. Fatigue fractures occur when an implant is loaded repetitively and may occur if delayed union is present. These fatigue fractures are also fostered by scratches, notches and the like. The specific design of our implant and its associated instrumentation minimizes the possibility of such fractures.

We Claim:

1. A surgical implant system for use in repair of fractures of the hip comprising a one-piece implant having an integral hip nail portion and bone plate portion, said portions being disposed at an obtuse angle relative to each other, said hip nail portion being of solid construction throughout and provided with a plurality of longitudinal flutes on its surface each terminating in a sharp cutting point and adapted to be driven into the proximal extremity of the femur, said bone plate being elongated having a concave inner surface and adapted to rest against the outer shaft of the femur, said hip nail portion and said bone plate portion terminating at a widened junction area, an impactor/extractor tool, means on the junction area for attachment of one end of said tool, means on the other end of said tool adapted to receive impact and extractive forces to force said hip nail portion into the femur, and a bone plate clamping tool for holding the bone plate portion against the femur shaft, said bone plate portion having at least one buttress on the outer surface thereof, means on said last named tool adapted to fit in said buttress, a clamp means on said last-named tool, and means to apply force to said clamp means and said means fitted in said buttress to move the same towards each other in clamping relation.

2. A one-piece surgical implant for use in repair of fractures of the hip comprising a hip nail portion and a bone plate portion depending therefrom at an obtuse angle, said hip nail portion being solid throughout its length and having a plurality of flutes extending longitudinally thereof along substantially the entire length of the nail portion, said flutes terminating in sharp pointed porjections adapted to cut into the bone, said bone plate portion having screw receiving holes therein for securing the same to the shaft of a femur, said hip nail portion and said bone plate portion joining at a junction area which is wider than said hip nail portion to accommodate extractor and impactor instrumentation.

3. An implant as defined in claim 2 and further including a blunt end projection extending from the end of said hip nail portion beyond said pointed projections and having a smaller cross-section than the cross-section of the fluted nail portion.

4. An implant as defined in claim 2 wherein said bone plate portion is provided with a concave inner face and a convex outer face.

5. An implant as defined in claim 4 wherein said bone plate portion is tapered from its juncture with the hip nail portion to its free end.

6. An implant as defined in claim 4, and further including at least one hemispherical recess on its outer convex face adapted to receive a clamping tool.

7. An implant as defined in claim 2 and further including a pair of impactor tool receiving buttresses formed on the sides of the implant at the widened junction between said hip nail portion and said bone plate portion, said buttresses having a rounded front abutment face and being open at the rear, said buttresses extending parallel to the axis of said hip nail portion.

8. An implant as defined in claim 7 and further including a pair of extractor tool receiving buttresses formed on the sides of the implant at the said widened junction, said extractor buttresses having a rounded rear abutment face spaced forwardly of and spaced slightly from the front abutment faces of said impactor buttresses, said extractor buttresses extending parallel to the axis of said hip nail portion.

9. An implant as defined in claim 8 wherein the extractor buttresses are open at their forward ends.

10. An impactor/extractor tool for attachment to a surgical hip nail implant to assist in insertion and extraction of said implant in a bone, said tool comprising a pair of spaced elongated arms, block means joining one end of each arm to the other and adapted to receive impact hammer blows, inwardly directed stub means adjacent the free ends of arms adapted to engage in buttresses provided on an implant, and means intermediate the ends of said arms for moving the same toward each other to engage said stub means in said buttresses.

11. An impactor/extractor tool as defined in claim 10 and further including impact receiving post means extending vertically from said block means.

12. An impactor/extractor tool as defined in claim 10 wherein the means for moving said arms consists of internally threaded means on one arm and a screw member passing through said other arm and threadedly engaged in said internally threaded means.

13. An impactor/extractor tool as defined in claim 11 wherein said stub means comprises a pair of extractor stubs of generally semicylindrical shape mounted on the free end of said arms and directed inwardly toward each other and a pair of impactor stubs on said arms spaced rearwardly of the extractor stubs.

14. An impactor/extractor tool as defined in claim 13 wherein the arms are formed from a spring metal and are secured to said block means at a diverging angle to each other.

* * * * *

UNITED STATES PATENT AND TRADEMARK OFFICE
CERTIFICATE OF CORRECTION

PATENT NO. : 4,009,712

DATED : March 1, 1977

INVENTOR(S) : Albert H. Burstein and Kingsbury G. Heiple

It is certified that error appears in the above-identified patent and that said Letters Patent are hereby corrected as shown below:

Column 4, line 6, change "4v" to -- 4V --;
         line 8, delete "6";
Claim 2, line 8, change "porjections" to -- projections --.

Signed and Sealed this

Twenty-fourth Day of May 1977

[SEAL]

Attest:

RUTH C. MASON
*Attesting Officer*

C. MARSHALL DANN
*Commissioner of Patents and Trademarks*